(12) United States Patent
Doerrich et al.

(10) Patent No.: US 10,351,747 B2
(45) Date of Patent: Jul. 16, 2019

(54) BRANCHED ORGANOSILOXANES USED AS HEAT TRANSFER FLUID

(71) Applicant: Wacker Chemie AG, Munich (DE)

(72) Inventors: Steffen Doerrich, Munich (DE); Richard Weidner, Burghausen (DE); Sven Heidsieck, Aalen (DE); Bernhard Rieger, Elchingen (DE)

(73) Assignee: Wacker Chemie AG, Munich (DE)

( * ) Notice: Subject to any disclaimer, the term of this patent is extended or adjusted under 35 U.S.C. 154(b) by 120 days.

(21) Appl. No.: 15/544,122

(22) PCT Filed: Jan. 26, 2016

(86) PCT No.: PCT/EP2016/051529
§ 371 (c)(1),
(2) Date: Jul. 17, 2017

(87) PCT Pub. No.: WO2016/124439
PCT Pub. Date: Aug. 11, 2016

(65) Prior Publication Data
US 2018/0010027 A1    Jan. 11, 2018

(30) Foreign Application Priority Data

Feb. 6, 2015  (DE) .................. 10 2015 202 158

(51) Int. Cl.
| | | |
|---|---|---|
| C09K 5/10 | (2006.01) | |
| C07F 7/08 | (2006.01) | |
| F24S 80/20 | (2018.01) | |
| B82Y 30/00 | (2011.01) | |

(52) U.S. Cl.
CPC ................ C09K 5/10 (2013.01); B82Y 30/00 (2013.01); C07F 7/0838 (2013.01); F24S 80/20 (2018.05); *Y02E 10/40* (2013.01)

(58) Field of Classification Search
CPC .......................................................... C09K 5/10
USPC ........................................................ 252/75
See application file for complete search history.

(56) References Cited

U.S. PATENT DOCUMENTS

| | | | |
|---|---|---|---|
| 4,122,109 A | 10/1978 | Halm | |
| 4,193,885 A | 3/1980 | Halm | |
| 9,267,067 B2 * | 2/2016 | Yang | C09K 5/10 |
| 10,150,902 B2 * | 12/2018 | Kato | H01L 23/373 |
| 2006/0051639 A1 * | 3/2006 | Yang | C09K 5/10 |
| | | | 429/437 |
| 2011/0172132 A1 * | 7/2011 | Branson | B82Y 30/00 |
| | | | 508/126 |
| 2012/0270129 A1 * | 10/2012 | Marinho | C09K 5/10 |
| | | | 429/434 |
| 2013/0269682 A1 | 10/2013 | Cuthbert et al. | |
| 2015/0175868 A1 * | 6/2015 | Hoffmann | C07F 7/21 |
| | | | 252/78.3 |

FOREIGN PATENT DOCUMENTS

| | | |
|---|---|---|
| DE | 2754705 A1 | 6/1978 |
| DE | 102012211258 A1 | 1/2014 |
| EP | 1473346 B1 | 5/2006 |
| GB | 586187 A | 3/1947 |
| GB | 627136 A | 7/1949 |
| JP | 2013545064 A | 12/2013 |
| RU | 2221826 C1 | 1/2004 |
| WO | 2010103103 A1 | 9/2010 |
| WO | 2013151601 A2 | 10/2013 |

OTHER PUBLICATIONS

DeBurgomaster et al. (2011). Rational tailoring of functional siloxanes for enhanced thermal performance. Presentation at the American Chemical Society National Meeting in Anaheim, CA. pp. 1-22.
Dow Chemical Company (1997). Syltherm 800: Heat Transfer Fluid. Product Technical Data. pp. 1-28.
English language abstract for RU 2221826 (2003).
English language abstract for DE 2754705 A1 (1978).
English language abstract for WO 2010103103 A1 (2010).
International Search Report from corresponding PCT/EP2016/051529 dated Apr. 7, 2016.

* cited by examiner

*Primary Examiner* — Jane L Stanley

(74) *Attorney, Agent, or Firm* — Caesar Rivise, PC

(57) ABSTRACT

The invention relates to a method for operating a system at an operating temperature of between 300° C. and 500° C., using a heat transfer fluid comprising branched siloxanes of general formula (I) $(R_3SiO_{1/2})_w(SiO_{4/2})_z$ in which w represents integral values of between 4 and 20, z represents integral values of between 1 and 15, and R represents a methyl group, the sum of the fractions of all siloxanes of general formula (1) being at least 95 mass %, in relation to the whole heat transfer fluid.

9 Claims, No Drawings

BRANCHED ORGANOSILOXANES USED AS HEAT TRANSFER FLUID

CROSS-REFERENCE TO RELATED APPLICATIONS

This application is a U.S. National Phase Application of PCT/EP2016/051529, filed Jan. 26, 2016, which claims priority from DE 10 2015 202 158.0, filed Feb. 6, 2015, the contents of which applications are incorporated herein by reference in their entireties for all purposes.

BACKGROUND OF THE INVENTION

The present invention relates to a method of operating a system using a heat transfer fluid comprising branched siloxanes.

Organosiloxanes and organopolysiloxanes (silicone oils), hereinafter referred to in short as "siloxanes", have thermal stability, a wide liquid range and a low temperature dependence for their viscosity and therefore are widely used as heat transfer fluids. DE 2754705 A1 sets out the advantages of siloxanes over other heat transfer media. It is especially at very low temperatures (below −50° C.) or very high temperatures (200-450° C.) that they are superior to organic heat transfer fluids or are the solely usable nonionic heat transfer fluid at all. EP 1473346 B1 for example describes mixtures of linear and cyclic dimethylpolysiloxanes that are usable as a refrigerant down to −100° C. Furthermore, the brochure "SYLTHERM 800 Heat Transfer Fluid—Product Technical Data" from The Dow Chemical Company (CH 153-046-E-1097, October 1997) describes a linear, permethylated silicone oil ("Syltherm 800") and reports the upper sustained use temperature to be 400° C. (closed loop, air excluded). It is further reported there that brief thermal aging up to 538° C. is achievable without appreciable decomposition.

The recited properties of siloxanes predestine their use as high temperature heat transfer fluids, for example in heat transfer systems, such as solar thermal power plants, especially in those with parabolic trough and Fresnel technology, where the heat transfer fluid is over many years exposed to high thermal aging up to 400° C. and substantial temperature variations. The use of silicone oils in solar thermal devices is described in DE 2754705 A1, U.S. Pat. Nos. 4,122,109 and 4,193,885.

WO 10103103 describes the use of polyorganosiloxanes as heat transfer fluid subject to the proviso that at least one organic moiety attached to the silicon has two carbon atoms. This fact is very disadvantageous for the use of siloxanes, since the heat transfer oil decomposes by β-H elimination when exposed to comparatively high thermal aging. Solely siloxanes without hydrogen atom β-positioned relative to the silicon are therefore suitable in a comparatively high temperature range.

The composition of siloxane mixtures is subject to rearrangement processes (equilibration) and so is temperature dependent and thereby also time dependent until equilibrium has been reached at the particular choice of temperature. Linear, permethylated silicone oils may need a few days to reach the equilibrium state, which is a mixture of linear and cyclic siloxanes, at 400° C. for example. The physical properties accordingly also change concurrently with the abovementioned process. The possible consequence is an appreciable change over time in important operating parameters of a device operated with siloxanes as heat transfer fluid, examples being the vapor pressure or the viscosity. This is disadvantageous because it may necessitate additional control engineering requirements or even extra capital expenditure to design and construct the device, or but limited utility or even complete inutility of the device over this period. The resultant cyclic siloxanes (inter alia D4) are undesirable because of their environmental and safety classifications.

The above-described rearrangement processes aside, the structure of linear siloxanes changes through disproportionation reactions. Disproportionation of linear chain members $R_2SiO_{2/2}$/D group leads to the formation of $RSiO_{3/2}$/T and $R_3SiO_{1/2}$/M groups. The T groups formed are branching sites in the siloxane structure and these branchings occasion a change in the physical properties of silicone oils such as, for example, an increase in viscosity, leading to an increased level of pumping needed in order to derive from the fluid the required amount of heat. This makes the systems difficult and eventually impossible to operate.

U.S. Pat. Nos. 4,122,109 and 4,193,885 describe the addition of metal-containing stabilizers and optionally also of hydrogen-containing silicon compounds to noncyclic methylpolysiloxanes in order to eliminate the temperature-dependent change in chemical composition and thus keep the composition, and the physical properties, stable over time. However, it is clear from the examples that rearrangements cannot be fully eliminated. The fluid is reported in the related product brochure ("Syltherm 800"), mentioned above, to undergo very slow rearrangement, the equilibrium state eventually being reached after some months. This is associated with an appreciable increase in the vapor pressure. Yet since, for cost reasons, heat transfer fluids do service in solar thermal power plants for years, stabilizer addition is thus unsuitable for this application because it is in any case unable to prevent the rearrangements during this period and is even disadvantageous by dint of the increased costs for material. Nothing is said about the stabilizers influencing the disproportionation reactions.

DE 102012211258 discloses that certain mixtures of siloxanes (mixtures of linear and cyclic siloxanes) are capable of having substantially unchanging physical properties over time on thermal aging at a constant temperature even though their chemical composition changes over time until the equilibrium state. In effect, the composition of these siloxane mixtures need not correspond to the equilibrium composition at that temperature. However, disproportionation reactions cannot be eliminated in such siloxane mixtures. In addition, cyclic siloxanes (inter alia D4) are undesirable because of their environmental and safety classifications.

RU 2221826 describes the use of mixtures of linear siloxanes, especially decamethyltetrasiloxane, and branched methylsiloxanes, especially methyl(trimethylsiloxy)silane as heat transfer medium for application in a temperature range of −135° C. to 120° C. Such a low temperature range is unlikely to result in a noticeable rate of the equilibration and disproportionation.

The invention provides a method of operating a system at an operating temperature of 300° C. to 500° C. using a heat transfer fluid comprising branched siloxanes of general formula I $$(R_3SiO_{1/2})_w(SiO_{4/2})_z \tag{I}$$

where
w represents integer values from 4 to 20,
z represents integer values from 1 to 15,
R represents methyl, wherein the sum total of the proportions of all siloxanes of general formulae I is not less than 95% by mass, based on the heat transfer fluid as a whole.

The $(R_3SiO_{1/2})_w$ and $(SiO_{4/2})_z$ units are known respectively as M groups and as Q groups.

Siloxanes subjected to thermal aging undergo disproportionation reactions and relatively slow reversible rearrangement processes to form, in a temperature and time dependent manner, an equilibrium state between various siloxanes. The resultant change in physical properties over time at constant temperature is disadvantageous for the application of siloxanes as heat transfer media. The invention rests on the discovery that both the mechanisms are distinctly more pronounced with linear, i.e., predominantly D-containing siloxanes, than with branched, i.e., Q-containing siloxanes. The siloxanes of general formula I and their mixtures have substantially unchanging physical properties over time.

DESCRIPTION OF THE INVENTION

The 25° C. viscosity of siloxanes of general formula I is preferably below 100 mPa*s, more preferably below 20 mPa*s and most preferably below 10 mPa*s, all measured using a µVISK viscometer from RheoSense Inc.

The vapor pressure of siloxanes of general formula I in service as a heat transfer fluid at operating temperature is preferably below 100 bar, more preferably below 50 bar and most preferably below 35 bar.

The siloxanes of general formula I may also contain, as a consequence of their method of synthesis, an R in the form of OH (silanol), $OR^2$ (alkoxy; $R^2$=alkyl), $OC(O)R^2$ (carboxyl; $R^2$=alkyl) and halogens. The proportion of silanol, alkoxy and halogen moieties is preferably low, more preferably below 0.5%. There are no silanol, alkoxy and halogen moieties in a preferred embodiment.

w preferably represents integer values up to 15.

z preferably represents integer 1 to 5.

w+z preferably represents values up to 50, especially up to 20.

Preference is given to mixtures where w represents values from 4 to 10 and z represents values from 1 to 4. Particular preference is given to mixtures where w represents values from 4 to 6 and z represents values from 1 to 2. The branched siloxane where w represents 4 and z represents 1 is especially preferable.

The siloxanes of general formula I may be in a monomodal, bimodal or multimodal form of molar mass distribution, at the same time the molar mass distribution may be narrow or broad.

The heat transfer fluids preferably contain less than 1000 ppm of water, more preferably contain less than 500 ppm of water and most preferably contain less than 200 ppm of water, all based on mass.

The degree to which the physical properties selected from density, vapor pressure, viscosity, heat capacity and thermal conductivity of the siloxanes of general formula I change in operation, more particularly the degree to which all these properties change in the course of the intended use, amounts to not more than 15%, preferably to not more than 10% and more preferably to not more than 5%.

The siloxanes of general formula I are obtainable via literature known methods of synthesis or via novel syntheses described in the examples.

The mixtures of siloxanes of general formula I are also obtainable by pure siloxanes of general formulae I, or any desired mixtures of such siloxanes, being prepared, mixed and added to one another in any order, optionally also repeatedly more than once, optionally also alternatingly or simultaneously. Suitable methods, distillation is an example, enable siloxanes or siloxane mixtures also to be removed again. The composition of the siloxanes of general formula I is controlled in the process through the amounts employed or removed for siloxanes of general formulae I. The method may be carried out at room temperature and ambient pressure, but also at elevated or reduced temperature and also elevated or reduced pressure.

Siloxanes of general formula I and mixtures thereof are further obtainable by suitable chlorosilanes, alkoxysilanes, silazanes, carboxysilanes or mixtures of said silanes being hydrolyzed or co-hydrolyzed and then freed of by-products such as hydrogen chloride, alcohols, ammonia, ammonium salts or carboxylic acids and if necessary also excess water. Optionally, the siloxane mixture obtained may have further siloxane added to it or removed via suitable methods, for example distillation. The method may be carried out at room temperature and ambient pressure, but also at elevated or reduced temperature and also elevated or reduced pressure. The composition of the siloxanes of general formula I and mixtures thereof is controlled in the process via the ratio between the amounts employed and perhaps removed again for silanes and/or siloxanes.

The siloxanes of general formula I and mixtures thereof are further obtainable by pure siloxanes of general formulae I, or any desired mixtures of such siloxanes, being equilibrated and/or endblocked to obtain siloxanes, and mixtures thereof, of changed composition. This composition may but need not correspond to the equilibrium composition. The method may be carried out at ambient pressure, but also at elevated or reduced pressure. Said equilibration may take place without a catalyst or in the presence of a homogeneous or heterogeneous catalyst, for example an acid or a base. The catalyst may thereafter be deactivated or removed from the siloxane and its mixture, for example by distillation or filtration, but need not. To avoid silanol groups in the siloxanes, these may be endblocked. Said endblocking may be carried out by usage of homogeneous or heterogeneous catalysts, for example an acid/Lewis acid, by reaction with $Me_3Si$—X (X=Cl, OH, OM (M=metal), H, $OSiMe_3$, $NHSiMe_3$), Me—Y (Y=halogen, OC(O)OMe, $OS(O)_2OMe$, M (M=metal), OH), $CH_2$=$N_2$ or a combination of said reagents. Endblocking with reagents may be carried out without a catalyst or in the presence of a homogeneous or heterogeneous catalyst, for example an acid/Lewis acid. The catalyst may thereafter be deactivated or removed from the siloxane and its mixture, for example by distillation or filtration, but need not.

It is also possible for siloxanes or siloxane mixtures to be removed again via suitable methods, for example distillation. The composition of the siloxanes of general formula I is controlled in the process via the ratio of the amounts employed and optionally removed again for siloxanes of general formulae I, the temperature and also the type (open or closed system) and duration of the equilibration and/or endblocking reaction.

The methods described above may also be combined. They may optionally be carried out in the presence of one or more solvents. The use of no solvent is preferred. The employed silanes, silane mixtures, siloxanes and siloxane mixtures are either standard products of the silicone industry or obtainable via known literature methods of synthesis. Further methods of synthesis are described in connection with the examples.

The heat transfer fluid may contain dissolved or suspended or emulsified additives to increase its stability or influence its physical properties as well as siloxanes of general formula I. Dissolved compounds of metals, for example iron carboxylates, may act as free-radical scavengers and oxidation inhibitors to enhance the durability of a heat transfer medium. Suspended additives, for example carbon or iron oxide, may improve physical properties of a heat transfer medium, for example the heat capacity or thermal conductivity.

The sum total of the proportions of all siloxanes of general formula I is preferably not less than 95% by mass, more preferably not less than 98% by mass and especially not less than 99.5% by mass, based on the heat transfer fluid as a whole.

The heat transfer fluids are preferably employed as high temperature heat transfer media in solar thermal devices, especially in parabolic trough and Fresnel power plants. They are further useful as heat transfer fluids in the chemical industry and also the metal, pharmaceutical and food industries, as heat transfer fluids for low temperatures and as working fluids in heat engines, especially but not exclusively solar thermal ones. The heat transfer fluids are more particularly used in concentrated solar power (CSP) power plants. The heat transfer fluids are preferably used at temperatures up to 490° C., especially 350° C. to 475° C., more preferably 400° C. to 450° C. At temperatures above 200° C., the use under a protective gas atmosphere is preferable in order to inhibit any oxidative decomposition. The protective gas used is preferably a noble gas, such as helium, argon or neon, or nitrogen.

The above symbols in the above formulae all have their meanings independently of each other in each case. The silicon atom is tetravalent in all the formulae.

In the examples which follow, amounts and percentages are all by weight, pressures are all 0.10 MPa (abs.) and temperatures are all 20° C., unless specifically stated otherwise.

EXAMPLES

General working techniques, solvents and chemicals Syntheses were all carried out under Schlenk conditions. The protective gas used was argon (99.998%, Westfalen AG). The chlorosilanes used were obtained from Wacker Chemie AG or from Sigma-Aldrich, fractionally distilled under reduced pressure before use, and stored under protective gas. The solvents used were conventionally dried and stored over activated molecular sieve (3 Å, VWR) and under argon. The drier used was sodium/diphenylmethanone for THF (tetrahydrofuran) and sodium for methanol. The other reagents and solvents were all acquired from ABCR, Sigma-Aldrich, Fluka or VWR and, unless otherwise stated, used without further purification. The water used was completely ion-free. KDS-200-CE syringe pump from KD Scientific was used for metered additions. To carry out the heat treatments, either 100 mg of the siloxane were fused under vacuum into a 1.5 ml prescored borosilicate glass ampoule (from Wheaton), or 1.5 g of the siloxane were introduced into a pressureproof 14 ml steel flask. The filling of the steel flasks was carried out in a suitably equipped glovebox (argon) from MBraun, into and out of which all the components were imported and exported via a conventional load lock system. The flasks were closed with a screw lid. A sealing paste (WS 600, from WEKEM) was used as additional sealing aid for the screw thread. The final tightening of the lid was done using a spanner after exporting the flasks out of the glovebox. The thermal aging of the siloxanes was effected by storing the filled glass ampoules or steel flasks in Carbolite LHT ovens from Carbolite GmbH at different temperatures in order to show the effects of the method according to the invention.

Samples were taken and analyzed by NMR spectroscopy, gas chromatography or dynamic viscometry. Comparative analyses of NMR measurements (mol %) and GC measurements (GC area %) display very good agreements, which is why data is entirely reported in % in the experimental section.

Analysis

Nuclear magnetic resonance spectra were recorded on a Bruker Avance I 360 ($^1$H: 360.1 MHz, $^{29}$Si: 71.6 MHz) spectrometer or a Bruker Avance III HD 500 ($^{29}$Si: 99.4 MHz) spectrometer using a BBO 500 MHz S2 probe head. Chemical shifts are reported in δ values (ppm) relative to the residual proton signal of the deuterated solvent used (Eurisotop) (CDCl$_3$, δ=7.26 ppm; CD$_2$Cl$_2$, δ=7.24 ppm). The internal reference used for the $^{29}$Si spectra was tetramethylsilane ($^{29}$Si: δ=0.00 ppm). Multiplicity of signals was abbreviated as follows: s (singlet), t (triplet) and q (quadruplet). The $^{29}$Si spectra were recorded using the INEPT pulse sequence for monomeric products of synthesis and using the inverse gated pulse sequence (NS=3000; 150 mg of siloxane in 500 μl of a 4×10$^{-2}$ molar solution of Cr(acac)$_3$ in CD$_2$Cl$_2$) for oligomeric products of synthesis. The glass hump was removed from the spectrum using the cryoprogld software package from Bruker. The GC/MS analysis was carried out on a Varian GC-3900 gas chromatograph (column: VF-5ms, 30 m×0.25 mm×0.25 μm, carrier gas: helium, flow rate: 1 ml/min, injector: CP-1177, split: 1:50) coupled to a Varian MS Saturn 2100 T (EI, 70 eV) mass spectrometer. The GC analysis was carried out using a Varian GC-3900 gas chromatograph (column: VF-200ms, 30 m×0.32 mm×0.25 μm, carrier gas helium, flow rate: 1 ml/min, injector: CP-1177, split: 1:50, detector: FID 39X1, 250° C.). Elemental analyses were carried out using a Vario EL analyzer from Elementar. Viscosity was determined at a temperature of 25° C. using a pVISK viscometer from RheoSense Inc. A B-580 ball tube oven from Buchi was used for the kugelrohr ball tube distillations. Reported temperatures correspond to the internal temperature of the oven.

Measurement of D and T Group Contents ($^{29}$Si NMR)

The extent of disproportionation (D or T group content) was determined using nuclear magnetic resonance spectroscopy ($^{29}$Si NMR; Bruker Avance III HD 500 ($^{29}$5i: 99.4 MHz) spectrometer using a BBO 500 MHz S2 probe head; inverse gated pulse sequence (NS=3000); 150 mg of siloxane in 500 μl of a 4×10$^{-2}$ molar solution of Cr(acac)$_3$ in CD$_2$Cl$_2$. The glass hump was removed from the spectrum using the cryoprogld software package from Bruker. For this, the integral of the D and T values was set in relation to the overall sum of the integral values for S groups (free silanes (e.g., Me$_4$Si or polymer-incorporated groups C$_4$Si), M groups (chain ends Me$_3$SiO$_{1/2}$— or C$_3$SiO$_{1/2}$), D groups (chain members —Me$_2$SiO$_{2/2}$— or C$_2$SiO$_{2/2}$), T groups (branch points MeSiO$_{3/2}$) and Q groups (crosslink points SiO$_{4/2}$) to give % D and % T respectively. Disproportionation leads to the conversion of 2M→S+D and of 2D→M+T. Therefore, the degree of disproportionation was judged by the proportion of T units on proceeding from DM systems and by the proportion of D units on proceeding from TM and QM systems.

Syntheses

Methyltris(trimethylsiloxy)silane (TM$_3$) (Not Inventive)

Methyltris(trimethylsiloxy)silane (TM$_3$) was prepared as described in EP1481979. Boiling point: 145° C., 20 mbar; $^1$H NMR (360.1 MHz, CDCl$_3$): δ[ppm]=0.12 (s, 27H, (CH$_3$)$_3$SiO$_{1/2}$), 0.01 (s, 3H, CH$_3$SiO$_{3/2}$); $^{29}$Si NMR (71.6 MHz, CDCl$_3$): δ [ppm]=7.6 (s, (CH$_3$)$_3$SiO$_{1/2}$), −64.0 (s, CH$_3$SiO$_{3/2}$); MS: m/z (%)=295.0 (100) [M$^+$ —CH$_3$]; elemental analysis: reckoned (%) for C$_{10}$H$_{30}$O$_3$Si$_4$: C, 38.66, H, 9.73; observed: C, 38.42, H, 9.86; viscosity: 1.39 mPa*s (25° C.)

MT siloxane T$_1$M$_{1.2}$ (Not Inventive)

In an argon-inertized 1 1 2-neck Schlenk flask equipped with septum and gas outlet, 50.0 g (335 mmol) of trichloromethyl-silane and 116 g (1.07 mol) of chlorotrimethylsilane are dissolved in 400 ml of acetonitrile. A syringe pump is used to add 56.0 g (3.11 mol) of water at 0.20 ml/min and 20° C. under agitation by vigorous stirring. On completion of the addition, the reaction solution is stirred at 20° C. for 2 h, admixed with 168 ml of water and extracted with methyl tert-butyl ether (3×200 ml). The combined organic phases are washed neutral with 150 ml of saturated aqueous sodium bicarbonate solution, with water (3×200 ml) and with 50 ml of saturated sodium chloride solution, dried over sodium sulfate (~40 g) and filtered. The solvent is removed under reduced pressure and the residue obtained is admixed with 5.00 g (31.0 mmol) of hexamethyldisilazane and stirred at 20° C. for 12 h. Volatile compounds are subsequently removed under reduced pressure (3.10$^{-2}$ mbar, 25° C.) to obtain 54.0 g of the product as a colorless oil. $^{29}$Si NMR (99.4 MHz, CD$_2$Cl$_2$): M to T ratio 1.2:1; viscosity: 6.73 mPa*s (25° C.)

Tetrakis(trimethylsilyloxy)silane (QM$_4$)

An argon-inertized 2 1 4-neck round-bottom flask equipped with reflux condenser, thermometer and stirrer is initially charged with 649 g (4.02 mol) of hexamethyldisiloxane and 64.0 g (2.00 mol) of methanol, followed by cooling to below 10° C. with an icebath. 9.80 g (100 mmol H$_2$SO$_4$) of concentrated sulfuric acid are added over 15 min, followed by stirring at 10° C. for 30 min. Then, 152 g (999 mmol) of tetramethyl orthosilicate are added over 30 min and the reaction solution is stirred at 10° C. for 1 h. Following addition of 105 g (5.83 mol) of water, the reaction solution is stirred for 3 h at room temperature and then for 3 h under reflux. The reaction solution is admixed with 500 ml of 1 M aqueous sodium bicarbonate solution and stirred at 20° C. for 10 min and the aqueous phase is separated off. The organic phase is washed neutral with water (3×200 ml). Then, the organic phase is desolventized under reduced pressure and the residue is subjected to fractional distillation in vacuo to obtain 201 g (522 mmol, 52.3% yield) of product as colorless oil. Boiling point: 180° C., 42.0 mbar; $^1$H NMR (360.1 MHz, CDCl$_3$): δ [ppm]=0.10 (s, 36H, (CH$_3$)$_3$SiO$_{1/2}$); $^{29}$Si NMR (71.6 MHz, CDCl$_3$): δ [ppm]=8.5 (s, (CH$_3$)$_3$SiO$_{1/2}$), −104.7 (s, SiO$_{4/2}$); MS: m/z (%)=369.2 (100) [M$^+$ —CH$_3$]; elemental analysis: reckoned (%) for C$_{22}$H$_{36}$O$_4$Si$_5$: C, 37.45, H, 9.43; observed: C, 37.26, H, 9.56; viscosity: 2.71 mPa*s (25° C.)

Hexakis(trimethylsiloxy)disiloxane (Q$_2$M$_6$)

Step 1: Synthesis of Hexaethoxydisiloxane

In an argon-inertized 500 ml 2-neck Schlenk flask equipped with septum and reflux condenser, 62.5 g (300 mmol) of tetraethyl orthosilicate, 1.35 ml (74.9 mmol) of water and 1.25 ml of 6 N hydrochloric acid are dissolved in 200 ml of tetrahydrofuran and refluxed for 3 h. The solvent is removed under reduced pressure and the residue obtained is fractionally distilled under reduced pressure to obtain 3.80 g (11.1 mmol, 7.33% yield) of the product as colorless oil. Boiling point: 125° C., 10.0 mbar; $^1$H NMR (360.1 MHz, CDCl$_3$): δ [ppm]=3.88 (q, $^3$J(H,H)=7.0 Hz, 12H, OCH$_2$CH$_3$), 1.25 (t, $^3$J(H,H)=7.0 Hz, 18H, OCH$_2$CH$_3$); $^{29}$Si NMR (71.6 MHz, CDCl$_3$): δ [ppm]=−88.6 (s, (OEt)$_3$SiO$_{1/2}$); MS: m/z (%)=297.1 (100) [M$^+$ —OCH$_2$CH$_3$]; elemental analysis: reckoned (%) for C$_{12}$H$_{30}$O$_7$Si$_2$: C, 42.1, H, 8.83; observed: C, 35.5, H, 9.03.

Step 2: Synthesis of hexakis(trimethylsiloxy)disiloxane (Q$_2$M$_6$)

In a 25 ml round-bottom flask fitted with reflux condenser, 1.71 g (4.99 mmol) of hexaethoxydisiloxane and 4.16 g (31.5 mmol) of trimethylsilyl acetate are initially charged and admixed with 710 μl of concentrated hydrochloric acid. The reaction solution obtained heats up to about 50° C. Once the reaction solution has cooled down to 20° C., it is admixed with 50.0 ml of diethyl ether, washed with saturated sodium bicarbonate solution (2×50.0 ml) and water (50.0 ml), dried over sodium sulfate (~5 g) and filtered. The solvent is removed under reduced pressure and the residue obtained is admixed with 15.0 ml of methanol. The precipitate formed is filtered off, washed with cold methanol and purified by sublimation (60° C., 0.02 mbar) to obtain 670 mg (1.10 mmol, 22.0% yield) of the product as colorless solid. $^1$H NMR (360.1 MHz, CDCl$_3$): δ [ppm]=0.12 (s, 54H, (CH$_3$)$_3$SiO$_{1/2}$); $^{29}$Si NMR (71.6 MHz, CDCl$_3$): δ [ppm]=8.8 (s, (CH$_3$)$_3$SiO$_{1/2}$), −106.8 (s, SiO$_{4/2}$); MS: m/z (%)=591.2 (100) [M$^+$ —CH$_3$]; elemental analysis: reckoned (%) for C$_{18}$H$_{54}$O$_7$Si$_8$: C, 35.6, H, 8.96; observed: C, 35.55, H, 9.07.

MQ Silicone Oil Q$_3$M$_{3.7}$

In a 1 1 3-neck flask fitted with reflux condenser and dropping funnel, 20.0 g (118 mmol) of tetrachlorosilane are dissolved in 200 ml of tetrahydrofuran. A solution of 63.7 g (706 mol) of trimethylsilanol in 200 ml of tetrahydrofuran is added over 2 h. The reaction solution obtained is stirred under reflux for 3 h and at 20° C. for 17 h. 500 ml of 1 M aqueous sodium bicarbonate solution and 500 ml of diethyl ether are added, the resulting phases are separated and the aqueous phase is extracted with diethyl ether (3×50.0 ml). The combined organic phases are washed neutral with water, dried over sodium sulfate (~40 g) and filtered. The solvent, excess trimethylsilanol and hexamethyldisiloxane are removed under reduced pressure and the residue obtained is admixed with 5.00 g (31.0 mmol) of hexamethyldisilazane and stirred at 20° C. for 12 h. Volatile compounds are subsequently removed under reduced pressure (3.10$^{-2}$ mbar, 25° C.) to obtain 27.0 g of the product as a colorless oil. $^{29}$Si NMR (99.4 MHz, CD$_2$Cl$_2$): M to Q ratio 3.7:1; viscosity: 5.97 mPa*s (25° C.)

Heat Treatment: Siloxanes and Siloxane Mixtures with Minimal Rearrangement (Equilibration)

Example 1 Heating of WACKER AK 5 (D$_4$M$_1$) (Not Inventive)

1.5 g of WACKER AK 5 MD siloxane (viscosity: 5.33 mPa*s at 25° C.) is heated in a steel ampoule for 7 days.

Low boilers (M$_2$, MDM, D$_3$, D$_4$) before heating ($^{29}$Si NMR): 0%

Low boilers (M$_2$, MDM, D$_3$, D$_4$) after heating at 400° C. ($^{29}$Si NMR): 13.4%

Low boilers (M$_2$, MDM, D$_3$, D$_4$) after heating at 425° C. ($^{29}$Si NMR): 13.4%

Example 2 Heating of TM$_3$ (Not Inventive)

1.5 g of TM$_3$ MT siloxane (viscosity: 1.39 mPa*s at 25° C.) is heated in a steel ampoule for 7 days.

Low boilers (M$_2$) before heating ($^{29}$Si NMR): 0%

Low boilers (M$_2$) after heating at 400° C. ($^{29}$Si NMR): 4.7%

Low boilers (M$_2$) after heating at 425° C. ($^{29}$Si NMR): 4.9%

Example 3 Heating of $T_1M_{1.2}$ (Not Inventive)

1.5 g of $T_1M_{1.2}$ MT siloxane (viscosity: 6.73 mPa*s at 25° C.) is heated in a steel ampoule for 7 days.
Low boilers ($M_2$) before heating ($^{29}$Si NMR): 0%
Low boilers ($M_2$) after heating at 400° C. ($^{29}$Si NMR): 7.1%
Low boilers ($M_2$) after heating at 425° C. ($^{29}$Si NMR): 9.0%

Example 4 Heating of $QM_4$ 1.5 g of $QM_4$ MQ siloxane (viscosity: 2.71 mPa*s at 25° C.) is heated in a steel ampoule for 7 days.
Low boilers ($M_2$) before heating ($^{29}$Si NMR): 0%
Low boilers ($M_2$) after heating at 400° C. ($^{29}$Si NMR): 0.1%
Low boilers ($M_2$) after heating at 425° C. ($^{29}$Si NMR): 0.3%

Example 5 Heating of $Q_2M_6$ 100 mg of $Q_2M_6$ MQ siloxane is heated in a glass ampoule for 7 days.
Low boilers ($M_2$) before heating (GC): 0%
Low boilers ($M_2$) after heating at 400° C. (GC): 0.1%
Low boilers ($M_2$) after heating at 425° C. (GC): 0.2%

Example 6 Heating of $Q_1M_{3.7}$ 1.5 g of $Q_1M_{3.7}$ MQ siloxane (viscosity: 5.97 mPa*s at 25° C.) is heated in a steel ampoule for 7 days.
Low boilers ($M_2$) before heating ($^{29}$Si NMR): 0%
Low boilers ($M_2$) after heating at 400° C. ($^{29}$Si NMR): 0.3%
Low boilers ($M_2$) after heating at 425° C. ($^{29}$Si NMR): 0.4%

A comparison of Examples 1 to 6 demonstrates the present invention (table 1): TM siloxanes (Examples 2 and 3) show that the degree of rearrangement is less pronounced as compared with MD siloxanes (Example 1), resulting in the formation of significantly less by way of low boilers, which are largely responsible for the vapor pressure increase and the viscosity reduction. In the case of QM siloxanes (Examples 4 to 6), rearrangement is almost fully eliminated, which consequently results in the formation of almost no low boilers.

TABLE 1

Comparison of heat treatment experiments

| Siloxane | Low boilers after 7 d at 400° C. [%] | Low boilers after 7 d at 425° C. [%] |
|---|---|---|
| $D_4M_1$ (WACKER AK 5)* | 13.4 | 13.4 |
| $TM_3$* | 4.7 | 4.9 |
| $T_1M_{1.2}$* | 7.1 | 9.0 |
| $QM_4$ | 0.1 | 0.3 |
| $Q_2M_6$ | 0.1 | 0.2 |
| $Q_1M_{3.7}$ | 0.3 | 0.4 |

*not inventive

It transpires that rearrangement is reduced by avoidance of D units and use of T units and almost fully eliminated by avoidance of D and T units and use of Q units. The consequence is that the physical properties of the heat transfer oil, for example its viscosity—as evidenced by table 2—or its vapor pressure, change much less, if at all.

TABLE 2

Comparison of heat treatment experiments

| Siloxane | Viscosity [mPa*s] | Viscosity after 7 d at 400° C. absolute [mPa*s] and the relative change from initial viscosity [%] (in parentheses) | Viscosity after 7 d at 425° C. absolute [mPa*s] and the relative change from initial viscosity [%] (in parentheses) |
|---|---|---|---|
| $D_4M_1$ (WACKER AK 5)* | 5.33 | 3.15 (40.9) | 3.15 (40.9) |
| $QM_4$ | 2.71 | 2.71 (0) | 2.69 (0.7) |
| $Q_1M_{3.7}$ | 5.97 | 6.01 (0.7) | 6.05 (1.3) |

*not inventive

As a result, there is no need for additional control engineering requirements during operation of a heat transfer system or even extra capital expenditure to design and construct the device, or for but limited utility or even complete inutility of the device over this period. A further advantage of QM siloxanes is that, as compared with DM siloxanes such as WACKER AK 5, no cyclic D siloxanes (inter alia D4) are formed, which is of substantial advantage with regard to environmental and safety engineering aspects in particular.

Heat Treatment: Siloxanes and Siloxane Mixtures with Minimal Disproportionation

Example 7 Heating of WACKER AK 5 (Not Inventive)

1.5 g of WACKER AK 5 MD siloxane (viscosity: 5.33 mPa*s at 25° C.) is heated in a steel ampoule at 450° C. for 42 days.
Fraction of disproportionation product (T groups) before heating ($^{29}$Si NMR): 0%
Fraction of disproportionation product (T groups) after heating ($^{29}$Si NMR): 4.9% and 1.2% on standardization to the D starting ratio (D/M start ratio=4/1).

Example 8 Heating of $QM_4$ 1.5 g of $QM_4$ MQ siloxane (viscosity: 2.71 mPa*s at 25° C.) is heated in a steel ampoule at 450° C. for 42 days.
Fraction of disproportionation product (D groups) before heating ($^{29}$Si NMR): 0%
Fraction of disproportionation product (D groups) after heating ($^{29}$Si NMR): 1.9% and 0.5% on standardization to the M starting ratio (M/Q start ratio=4/1).

Example 9 Heating of $Q_1M_{3.7}$ 1.5 g of $4_1M_{3.7}$ MQ siloxane (viscosity: 5.97 mPa*s at 25° C.) is heated in a steel ampoule at 450° C. for 42 days.
Fraction of disproportionation product (D groups) before heating ($^{29}$Si NMR): 0%
Fraction of disproportionation product (D groups) after heating ($^{29}$Si NMR): 2.2% and 0.6% on standardization to the M starting ratio (M/Q start ratio=3.7/1).

A comparison of Examples 7 to 9 demonstrates the present invention (table 3): QM siloxanes (Examples 8 and 9) show that the extent of disproportionation is less pronounced as compared with MD siloxanes (Example 7) and as a result the numbers of chain ends (M), the linear chain members (D), the branch points (T) and the crosslink points (Q) change less, the consequence of which is that the physical properties of the heat transfer oil, for example its vapor pressure or its viscosity, change to a significantly smaller degree. As a result, there is no need for additional control engineering requirements during operation of a heat transfer system or even extra capital expenditure to design and construct the device, or for but limited utility or even complete inutility of the device over this period. A reduced extent of disproportionation extends the service life and reduces the exchange rate of the heat transfer oil, as a result of which the operation of heat transfer systems becomes significantly more economical. The lower rate of disproportionation means that the heat transfer oil can also be used at higher operating temperatures than MD siloxanes, as a result of which higher heat transfer efficiencies are attained in solar thermal systems for example. This leads to a distinctly enhanced efficiency and more economical operation of heat engines.

TABLE 3

Comparison of heat treatment experiments

| Siloxane | Fraction of disproportionation product after 42 d at 450° C. [%] | Fraction of disproportionation product after 42 d at 450° C. [%] as standardized to the starting ratio |
|---|---|---|
| $D_4M_1$ (WACKER AK 5)* | 4.9 | 1.2 |
| $QM_4$ | 1.9 | 0.5 |
| $Q_1M_{3.7}$ | 2.2 | 0.6 |

*not inventive

What is claimed is:

1. A method of operating a system at an operating temperature of 300° C. to 500° C. using a siloxane-based heat transfer fluid, said method comprising providing in the system a heat transfer fluid comprising branched siloxanes of general formula I $$(R_3SiO_{1/2})_w(SiO_{4/2})_z, \quad (I)$$

where
  w represents integer values from 4 to 10,
  z represents integer values from 1 to 4,
  R represents methyl,
  wherein
    a sum total of proportions of all siloxanes of general formula I is not less than 99.5% by mass, based on the heat transfer fluid as a whole.

2. The method as claimed in claim 1 wherein w represents 4 and z represents 1.

3. The method as claimed in claim 2 wherein the heat transfer fluid contains dissolved suspended or emulsified additives as well as siloxanes of general formula I.

4. The method as claimed in claim 3 wherein the sum total of the proportions of all siloxanes of general formula I is not less than 99.5% by mass, based on the heat transfer fluid as a whole.

5. The method as claimed in claim 4 wherein the system is a solar thermal device.

6. The method as claimed in claim 5 wherein the system is a concentrated solar power (CSP) power plant.

7. The method as claimed in claim 1 wherein the heat transfer fluid contains dissolved, suspended or emulsified additives as well as siloxanes of general formula I.

8. The method as claimed in claim 1 wherein the system is a solar thermal device.

9. The method as claimed in claim 8 wherein the system is a concentrated solar power (CSP) power plant.

* * * * *